(12) United States Patent
Pyles et al.

(10) Patent No.: US 6,509,020 B1
(45) Date of Patent: Jan. 21, 2003

(54) REPLICATION-COMPETENT HERPES SIMPLEX VIRUS

(75) Inventors: Richard Brent Pyles, Cincinnati, OH (US); Linda Marie Parysek, Cincinnati, OH (US); Ronald E. Warnick, Loveland, OH (US)

(73) Assignee: The University of Cincinnati, Cincinnati, OH (US)

( * ) Notice: Subject to any disclaimer, the term of this patent is extended or adjusted under 35 U.S.C. 154(b) by 0 days.

(21) Appl. No.: 09/381,733

(22) PCT Filed: Mar. 27, 1998

(86) PCT No.: PCT/US98/06124

§ 371 (c)(1),
(2), (4) Date: May 2, 2000

(87) PCT Pub. No.: WO98/42195

PCT Pub. Date: Oct. 1, 1998

Related U.S. Application Data

(60) Provisional application No. 60/042,418, filed on Mar. 27, 1997, now abandoned.

(51) Int. Cl.[7] ............... A61K 39/12; C12N 13/00; C12N 15/00; C12P 21/06
(52) U.S. Cl. ............... 424/231.1; 424/199.1; 424/205.1; 435/5; 435/320.1; 435/173.3; 435/69.1; 536/23.72
(58) Field of Search ............... 424/199.1, 231.1, 424/205.1; 435/173.3, 69.1, 320.1, 5; 536/23.72

(56) References Cited

U.S. PATENT DOCUMENTS 5,328,688 A 7/1994 Roizman ............... 424/205.1
5,585,096 A 12/1996 Martuza et al. ............ 424/93.2

OTHER PUBLICATIONS

Mullaney et al. J. Gen. Virology, vol. 70, pp. 449–454, 1989.*
Mineta et al. Nature Medicine, vol. 1, No. 9, pp. 938–943, 1995.*
Richard B. Pyles and Richard L. Thompson, *Evidence that the Herpes Simplex Virus Type 1 Uracil DNA Glycosylase is Required for Efficient Viral Replication and Latency in the Murine Nervous System*, Journal of Virology, Aug. 1994 pp. 4963–4972.
Thomas A. Winters and Marshall V. Williams, *Purification and Characterization of the Herpes Simplex Virus Type 2–Encoded Uracil–DNA Glycosylase*, Virology, 1993, vol. 195, pp. 314–326, abstract.
International Search Report of PCT/US98/06124, May 22, 1998, Jay Williams, (2 pages).

* cited by examiner

Primary Examiner—Ali R. Salimi
(74) Attorney, Agent, or Firm—Wood, Herron & Evans, L.L.P.

(57) ABSTRACT

A promising approach for the therapeutic treatment of brain tumors utilizes replication-competent, neuroattenuated herpes simplex virus-1 (HSV-1) mutants. This approach requires mutation of HSV-1 to eliminate killing of normal, non-dividing cells of the brain (e.g., neurons). The present invention discloses methods for killing malignant brain tumor cells in vivo entails providing replication competent herpes simplex virus vectors to tumor cells. A replication competent herpes simplex virus vector, with defective expression of the gamma 34.5 gene and the uracil DNA glycosylase (UNG) gene, specifically destroys tumor cells, is hypersensitive to anti-viral agents, and is not neurovirulent.

7 Claims, 7 Drawing Sheets

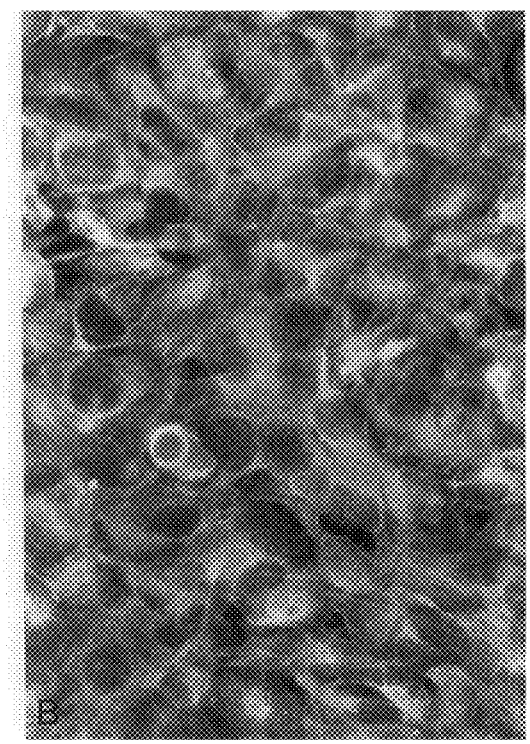
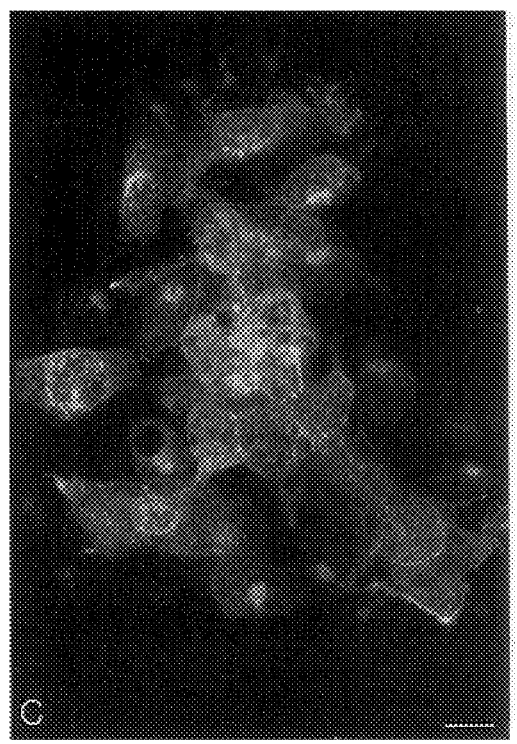
FIG. 3B
FIG. 3C
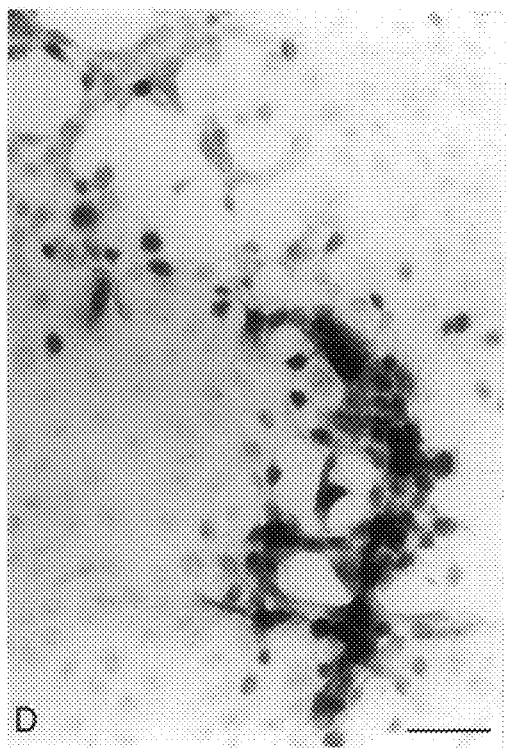
FIG. 3D

REPLICATION-COMPETENT HERPES SIMPLEX VIRUS

CROSS REFERENCE TO RELATED APPLICATIONS

This Application claims priority to PCT Application No. PCT/US98/06124 entitled "REPLICATION-COMPETENT HERPES SIMPLEX VIRUSES" and filed Mar. 27, 1998, now abandoned and U.S. Provisional application No. 60/042,418 filed Mar. 27, 1987.

This invention was made in part with Government support under Grant Nos. NS31145 and T32-CA59268 awarded by the National Institutes of Health. The Government may have certain rights in this invention.

FIELD OF THE INVENTION

The present invention relates to recombinant virus strains capable of killing tumor cells. More specifically, the present invention relates to a mutated replication-competent viruses which contains mutations in two genes, is hypersensitive to antiviral agents such as ganciclovir, is not neurovirulent and does not replicate in non-dividing cells, yet can kill nervous system tumor cells. The present invention also relates to recombinant herpesvirus strains, vital vaccines incorporating such strains, methods for making such strains and vaccines, and methods for immunizing a human host against herpes simplex virus using the vaccines.

DESCRIPTION OF THE RELATED ART

Malignant tumors of the nervous system are generally fatal, despite many recent advances in neurosurgical techniques, chemotherapy and radiotherapy. In particular, there is no standard therapeutic modality that has substantially changed the prognosis for patients diagnosed with malignant brain tumors. For example, high mortality rates persist in malignant medulloblastomas, malignant meningiomas and neurofibrosarcomas, as well as in malignant gliomas.

Gliomas are the most common primary tumors arising in the human brain. The most malignant glioma, the glioblastoma, represents 29% of all primary brain tumors, some 5,000 new cases per year in the United States alone. Glioblastomas are almost always fatal, with a median survival of less than a year and a 5-year survival of 5.5% or less. Mahaley et al., J. Neurosurg. 71: 826 (1989); Shapiro, et al., J. Neurosurg. 71: 1 (1989): Kim et al., J. Neurosurg. 74: 27 (1991). After glioblastomas are treated with radiotherapy, recurrent disease usually occurs locally; systemic metastases are rare. Hochberg et al., Neurology 30: 907 (1980). Neurologic dysfunction and death in an individual with glioblastoma is due to the local growth of the tumor.

Efforts to cure primary and metastatic brain tumors have focused on new approaches that make use of genetically modified viruses either to deliver cytotoxic genes to tumor cells or to directly infect and destroy tumor cells in a selective fashion. Treatment strategies employing replication-competent HSV-1 mutants may be particularly promising (Hum. Gene Ther. 5, 183–191; Cancer Res. 54, 5745–5751.; J Neuro-Oncol, 19, 137–147: J. Neurosurg, 77, 590–594: Neurosurg. 32, 597–602; Science 252, 854–856; Stereotact. Funct. Neurosurg. 59, 92–99; Nature Med. 1, 938–943; Virol. 211, 94–101.) Such mutants, like wild-type HSV-1 strains, establish a lytic infection in dividing tumor cells, leading to tumor cell destruction, but establish only a latent infection of the surrounding nondividing brain cells, including neurons. These mutants are attenuated human pathogens and thus, must be examined fully for their safety and utility prior to clinical use.

The first HSV-1 mutant studied, dlsptk, carried a single mutation in the thymidine kinase (TK) gene. Mutant strain dlsptk was found to have significant antineoplastic efficacy with a minimal level of toxicity in human tumor xenografts in immunodeficient mice (Neurosurg. 32, 597–602; Science 252, 854–856). These effects demonstrated the potential of HSV-1 as a tumor therapy, but at least two concerns regarding the safety of dlsptk limited its potential for human use. Because it lacks a functional TK gene, strain dlsptk cannot be controlled by the antiherpetic drugs acyclovir or ganciclovir. Second, infection with TK mutant strains causes neurovirulence in animal models when used at doses that would be employed for cancer therapy (N. Engl. J. Med. 320, 293–296). For these reasons, investigators have tested the usefulness of other mutations that severely reduce the ability of the virus to replicate in nondividing cells but do not prevent viral replication in actively dividing cells (Cancer Res. 54, 5745–5751: J Neuro-Oncol. 19, 137–147; J. Neurosurg. 77, 590–594; Neurosurg. 32, 597–602; Virol. 211, 94–101). One such mutation, introduced in both copies of the diploid ICP34.5 gene, has been shown in at least two parental HSV-1 backgrounds to result in viral vectors that have the tumor kill efficiency of dlsptk but minimal to no detectable toxicity (J. Neurosurg. 77, 590–594: Neurosurg. 32, 597–602; Virol. 211, 94–101. J. Gen. Virol. 75, 2059–2063.). Importantly, the HSV-1 strains with mutation of only the ICP34.5 genes retain TK activity, allowing for control by antiherpetic drugs that are activated by HSV-encoded TK. In U.S. Pat. No. 5,328,688. Roizman. issued Jul. 12, 1994, there is disclosed an HSV-1 strain that is reported to be rendered avirulent by the prevention of expression of an active product of a gene, designated gamma 34.5. that maps to the inverted repeats, flanking the long unique sequence of herpes simplex virus DNA. this gene is not essential for viral growth in cell culture. Viruses from which 34.5 was deleted or which carried premature stop codons in the 34.5 gene are avirulent following intracerebral inoculation of mice.

More recently, efforts to increase the safety of herpes-based therapy have spurred the development of HSV-1 strains that have mutations in two viral genes and thus are theoretically less likely to be repaired by recombination with a preexisting or subsequent HSV-1 infection. U.S. Pat. No. 5,585,096, Martuza et al., issued Dec. 17, 1996, discloses a method for killing malignant brain tumor cells in vivo by introducing replication-competent herpes simplex virus vectors to tumor cells. A replication-competent herpes simplex virus vector, with defective expression of the gamma 34.5 gene and the ribonucleotide reductase gene, specifically destroys tumor cells and is not neurovirulent.

Initial success with such a strain, designated G207, has been reported for treatment of glioblastoma xenografts established in immunodeficient mice (Nature Med. 1, 938–943). Strain G207 carries a deletion of both copies of the ICP34.5 gene and a mutated ICP6 gene, that encodes the large subunit of the ribonucleotide reductase, an enzyme in the salvage pathway required for efficient DNA synthesis (ROIZMAN, B. and SEARS. A. E., 1990). Herpes simplex viruses and their replication, p. 1795–1841. In B. N. Fields, et al. (ed.), Virology, 2nd ed. Raven Press, New York). In addition to being multiply-mutated, this virus also retains sensitivity to antiherpetic drugs and has minimal toxicity in animal models (Nature Med. 1, 938–943).

It remains of utmost importance to develop a multiple HSV-1 mutant viral strain that has the greatest possible safety and therapeutic value.

SUMMARY OF THE INVENTION

It is therefore an object of this invention to provide a replication-competent viral vector, suitable for use in humans, that is capable of killing human tumor cells in vivo, that exhibits hypersensitivity to anti-viral agents and an inability to revert to wild-type virus, and that is not neurovirulent at a dose required to kill tumor cells.

It is another object of the present invention to provide for the production of a replication-competent herpes simplex virus-derived vector that is effective and safe for use in the treatment of malignant brain tumors in humans.

It is a further object of the invention to provide a safe, mutated HSV-1 vector, incapable of reverting to wild-type form through a spontaneous single mutation, for use in the context of a vaccine or tumor therapy.

Still another object of the present invention is to provide a mutant HSV-1 vector that can selectively replicate in and kill a tumor cell of non-nervous tissue origin.

An additional object of the present invention is the production of a replication-competent viral vector, derived from herpes simplex virus, that can be employed in a genetic therapy against tumors by expressing foreign genes to target an immune response that kills the tumor cells.

Yet another object of the present invention is the production of a mutant herpes simplex virus vector containing a tumor cell-specific promoter so that the vector can be targeted to specific tumor cells.

It is also an object of the present invention to provide for production of a replication competent viral vector that is effective and safe for use as a vaccine to protect against infection by herpes simplex virus.

In satisfying these and other objects, there has been provided, in accordance with one aspect of the present invention, a replication-competent herpes simplex virus that is incapable of expressing both (i) a functional gamma 34.5 gene product and (ii) a uracil DNA glycosylase. In a preferred embodiment, the vector contains alterations in both genes.

In accordance with another aspect of the present invention, a method has been provided for killing tumor cells in a subject, comprising the step of administering to the subject a pharmaceutical composition comprising (A) a herpes simplex virus vector that is altered in (i) the gamma 34.5 gene, and (ii) the a uracil DNA glycosylase (UNG) gene; and (B) a pharmaceutically acceptable vehicle for the vector, such that the tumor cells are altered in situ by the vector and the tumor cells are killed. The tumor cells can be of a nervous-system type selected from the group consisting of astrocytoma, oligodendroglioma, meningioma, neurofibroma, glioblastoma, ependymoma, Schwannoma, neurofibrosarcoma, and medulloblastoma. Other kinds of tumor cells which can be killed, pursuant to the present invention, include those selected from the group consisting of melanoma cells, pancreatic cancer cells, prostate carcinoma cells, breast cancer cells, lung cancer cells, colon cancer cells lymphoma cells, hepatoma cells and mesothelioma and epidermoid carcinoma cells.

In accordance with still another aspect of the present invention, a method is provided for killing tumor cells in a subject, comprising the steps of administering to the subject a herpes simplex virus vector, wherein the vector comprises a tumor cell-specific promoter wherein the promoter controls expression of at least one viral protein necessary for viral replication and wherein the promoter is induced selectively or at a higher level in tumor cells than in normal cells. This method can entail the use of a promoter that is selectively capable of expression in nervous-system tumor cells, for example, glioblastoma cells, medulloblastoma cells, meningioma cells, neurofibrosarcoma cells, astrocytoma cells, oligodendroglioma cells, neurofibroma cells, ependymoma cells and Schwannoma cells.

A method also is provided for preparing a replication-competent vector of a herpes simplex virus, comprising the steps of (A) isolating a viral genome of the herpes simplex virus: and (B) permanently altering the genome so that the virus is (1) sensitive to antiviral agents, (2) kills tumor cells and (3) expresses decreased generalized neurovirulence. For example, the vector can be derived from either HSV-1 or HSV-2.

The present invention further provides for a method of protecting a subject against herpes simplex virus infection, comprising the step of administering to the subject a pharmaceutical composition that is comprised of (A) a herpes simplex virus vector wherein the genome of the virus is altered in (i) the gamma 34.5 gene, and (ii) the a uracil DNA glycosylase gene; and (B) a pharmaceutically acceptable vehicle for the vector.

According to still another aspect of the present invention, there has been provided a method of eliciting an immune response to a tumor cell, comprising the step of administering to the subject a pharmaceutical composition comprising (A) a herpes simplex virus, wherein the genome of the virus (i) contains an expressible non-herpes simplex virus nucleotide sequence encoding a desired protein capable of eliciting an immune response in the subject, and (ii) is altered in the gamma 34.5 gene, and the uracil DNA glycosylase gene: and (B) a pharmaceutically acceptable vehicle for the virus. In a preferred embodiment, the method further comprises the step of co-administration with neurosurgery, chemotherapy or radiotherapy.

Other objects, features and advantages of the present invention will become apparent from the following detailed description. It should be understood however, that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention can be understood more fully by reference to the following drawings, where.

Figure 1A:
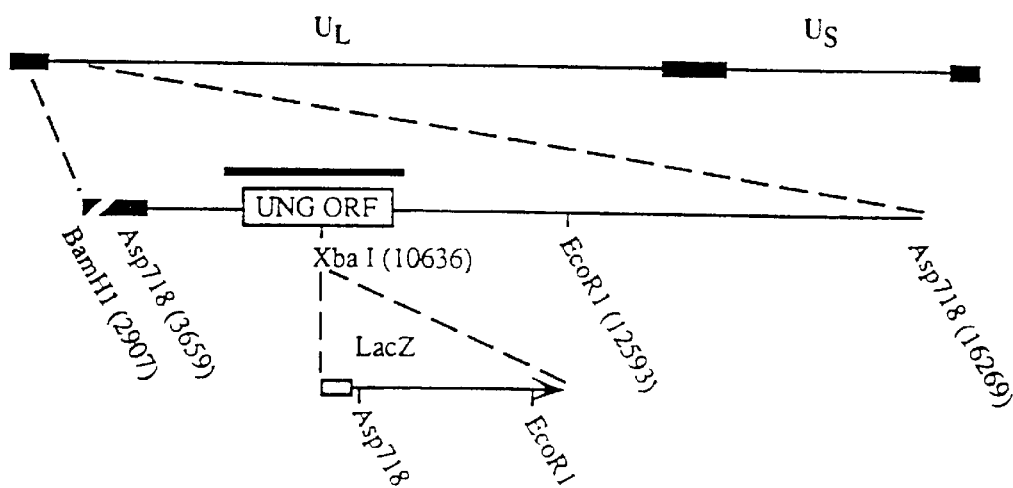
FIG. 1: Genomic Structure of HSV-1 Strain 3616UB.

Panel A. Top line: A schematic representation of the 152 kb wild type HSV-1 genome. The solid boxes represent the terminal and internal repeat elements of the HSV-1 genome. The unique long and unique short sequences are indicated by $U_L$ and $U_S$. Bottom line: Expansion of the left end of the genome beginning at the Bam H1 site at bp 2907 and extending to the Asp 718 site at bp 16269. The UNG open reading frame (ORF) and the position of the LacZ gene insertion in the UNG ORF is indicated. Panels B & C. Restriction enzyme digestion of 3616UB DNA with Eco R1 or Asp 718 followed by Southern analysis with a UL2 probe (panel B depicted by the solid box above the UNG ORF) spanning HSV-1 bps 8662–11820 or a Lac Z probe (panel C) indicates that the UNG gene in the 3616UB genome is interrupted by the LacZ gene. The structure of 3616UB (U) is compared to that of R3616 (R) and strain F (F) for each probe and each enzyme. Migration of the 12, 10, 8 and 6 kb DNA size markers (top to bottom) is indicated by dashes on each blot.

FIG. 2: The sensitivity of 3616UB to Ganciclovir (GCV).

Panel A graphically reports the results of exposure of infected VERO cultures to ganciclovir (GCV). The percent of surviving plaques represents the [(mean number of plaques in parallel cultures that were not exposed to GCV)/ (mean number of plaques from triplicate cultures following GCV exposure)]×100%. Panel B is a plaque reduction assay following exposure of infected cultures to increasing doses of GCV. The percent plaques represents [(the mean number of plaques from triplicate cultures exposed to the indicated dose of GCV)/(the mean plaques of parallel cultures not exposed to GCV)]×100%. The GCV doses that showed significantly greater inhibition of 3616UB compared to strain F are denoted by *.

FIG. 3: In vitro infection and killing of human tumor cell lines by 3616UB.

Panel A is a compilation of the killing of monolayers of tumor cells following infection with 1 3616UB PFU per 10,000 cells (MOI of 0.000 1). Following infection of duplicate monolayers, daily observations were made to estimate the percent of the monolayer showing virally-induced cytopathic effect as a measure of cell killing. To show that the observed cytopathic effect was due to infection by 3616UB, additional infected cultures of each cell line were fixed at 24 hours PI and immunostained for the presence of HSV-1 antigen. Strain 3616UB-infected DAOY monolayers are shown in panels B and C as a representative cell line. For visualization of uninfected cells, the cultures also were exposed to a monoclonal antibody to vimentin (panel B). The same field of DAOY cells immunofluorescently stained for HSV-1 proteins is shown in panel C. Those cells infected at 24 hours PI by 3616UB are demonstrated by reaction with the HSV antibodies. A similarly infected DAOY culture also Was histochemically stained for 3616UB-induced b-galactosidase activity. Cells infected by 3616UB turn blue after exposure to the chromagen X-gal (panel D). The bar in C is for B and C; bar=10 mm, Bar in D=50 mm.

FIG. 4: HSV-1 antigen production in infected primary neuronal cultures.

Primary rat neuronal cultures infected with either strain 3616UB (panels A and B) or strain F (panels C and D) were photomicrographed in phase (to visualize all neurons, panels A and C) and for immunofluorescent localization of HSV-1 proteins (to illustrate the infection of any neurons, panels B and D) at 6 days post infection. Panels A and B represent the same field of neurons infected with 3616UB showing no morphological changes or any HSV-1 proteins. Panels C and D show a similar neuronal culture infected with strain F to illustrate the presence of morphological changes and HSV proteins. The arrow in panel D indicates two neuronal cell bodies that were not infected by strain F. Panels B and D were generated using equivalent film exposure times, Bar= 50 mm.

FIG. 5: Localization of HSV-1 antigen in a medulloblastoma tumor xenog raft following injection of 3616UB.

Following xenograft formation, DAOY tumors were injected with 3616UB to determine if tumor cells were infected and if the virus spread through the tumor. After 48 hours, the animals were sacrificed and the tumors were stained for HSV-1 protein. Tumor cells that contained HSV-1 protein were found throughout the xenograft illustrating that 3616UB infected and spread through the xenograft. Two regions of HSV-1 infection from the same xenograft are shown in panels A and B. Panel A includes the needle track in the upper right corner, Bar=50 mm.

FIG. 6: HSV-1 treatment of human tumor xenografts established in severe-combined immunodeficient mice.

Panel A shows the results of two intratumoral injections, seven days apart, of $1\times10^6$ PFU/ml of 3616UB, $1\times10^6$ PFU/ml of R3616 or medium alone into human medulloblastoma xenografts of 50mm$^3$ initial volume. Groups of ten tumors were treated similarly and monitored for growth by measuring tumor volumes. Tumor volumes were determined at points after treatment were compared to the volume at the completion of treatment to establish growth ratios. Average growth ratios are plotted±SEM. Panel B presents a similar study of 3616UB efficacy in the faster growing human angiosarcoma tumor xenografts. Significant growth ratio differences (ANOVA p<0.01) between the treated and mock treated groups are denoted by *.

FIG. 7: HSV antigen production in normal murine brain following intracranial injection of strain 3616UB or F.

The needle track (top right corner) in a section of a SCID mouse brain that had been stereotactially injected with 3616UB, 48 hours prior, is presented in panel A. The section has been immunostained for the presence of HSV-1 protein and even after over-exposure of the film no HSV-1 proteins were evident. The needle track (top right corner) in a similar section from a SCID mouse injected with strain F, 24 hours prior, is shown in panel B. A large number of infected cells are clustered near the track (B) and spread of the virus is evident throughout the brain with concentrated areas of infected cells near white matter tracks and the ventricles. The arrows in panel B denote regions of strain F infection, Bar=100 mm.

DETAILED DESCRIPTION

The present invention provides mutant, replication-competent HSV-1 viruses that can enter a tumor cell in situ, make multiple copies, lyse the tumor cell and spread to additional tumor cells with relatively minor effects on the surrounding normal cells.

As used herein, the term "mutant" refers to a genetically altered or engineered virus that contains a purposefully introduced mutation. As used herein, the term "mutation" refers to a change in the chemistry of a gene, a change in the sequence of base pairs in the genomic molecule, that is perpetuated in subsequent progeny of the virus in which it occurs that results in a new species or strain, as distinguished from variation.

The mutant herpes simplex virus of the present invention has each of the following characteristics: (1) efficacy in killing human brain tumor cells, (2) marked attenuation of generalized neurovirulence to protect the normal brain, (3) multiple deletions so that a single mutation cannot cause reversion to the wild-type viral phenotype, and (4) hyper-sensitivity to an antiviral agent so that undesired spread of the virus can be prevented. The mutant virus of the present invention is capable of replicating in neoplastic cells, and lysing said neoplastic cell, but spares surrounding non-neoplastic tissue.

Viruses of the instant invention are engineered to contain alterations in the expression of at least two specific HSV-1 genes: (1) the gamma 34.5 gene and (2) the uracil DNA glycosylase gene. Alterations in this regard include any that disrupt the expression of the product of both the gamma 34.5 gene and the uracil DNA glycosylase gene. The presence of such multiple mutations further reduces the possibility of reversion to wild-type pathogenicity. The present invention provides methods for sequentially constructing and testing viruses for the ability to effectively kill brain tumor cells without harming surrounding normal brain. Additionally, mutations can be inserted into these vectors to increase their sensitivity to systemically administered drugs.

Herpes simplex virus UNG-mutants are severely compromised in their ability to productively infect nondividing cells in vivo, Pyles and Thompson, J. Virol. 68. Therefore, these mutants are attenuated for neurovirulence and less likely to propagate following reactivation signal such as fever or UV exposure. Such characteristics are essential to a therapeutic vector that must be of attenuated neurovirulence and amenable to antiviral therapy in the unexpected event of viral encephalitis.

Herpes simplex virus mutants deficient in only the gamma 34.5 gene, such as R3616, are attenuated for neurovirulence, which reduces the possible damage to normal brain cells. Goodman et al., J. Virol. 63: 1153 (1989); Chou et al., Science 250: 1262 (1990). The decreased neurovirulence of R3616 is putatively associated with the cessation of neuronal protein synthesis, preempted in wild-type herpes simplex virus infection. Chou and Roizman. Proc. Nat'l Acad. Sci. USA 89: 3266 (1992). The lack of 34.5 gene product leads to reduced viral replication in confluent primary cells. See Bolovan et al., J. Virol. 68: 48 (1994). The gamma 34.5 gene product can be detected by Western blot or ELISA analysis of infected cell proteins. The gamma 34.5 gene is also present in HSV-2. McGeoch et al., J. Gen. Virol. 72: 3057 (1991). The gamma 34.5 gene has been sequenced in four strains of HSV-1, namely F, 17, MGH-10 and CVG-2. Chou and Roizman. J. Virol. 64: 1014 (1990). The gamma 34.5 gene mutant HSV-1 vectors retain a wild-type level of sensitivity to acyclovir. Markert et al., supra (1993).

Mutants of gamma 34.5 have been constructed by various investigators using different techniques and in different strains such as mutant 1776 (McKie et al., J. Gen. Virol. 75: 733 (1994)] and 17termA [Bolovan et al., J. Virol. 68: 48 (1994)] in HSV-1 strain 17.

The present invention provides a novel alternative approach to eliminating the activity of a virally-encoded. DNA metabolism enzyme, by direct mutations to those viral functions involved in the editing of the viral DNA. Because the HSV-1 genome is composed of 75% guanosine and cytosine nucleotides, the uracil DNA glycosylase function is especially important for efficient viral progeny production. The UNG activity corrects misincorporated uracil events and potentially more importantly for HSV-1, the UNG activity removes uracils that arise by the spontaneous deamination of cytosine residues. Because non-dividing cells like neurons have insufficient levels of UNG activity, HSV-1 strains that replicate efficiently in neurons must encode there own. HSV-1 UNG-mutants are therefore reduced in their ability to cause neurovirulence. Pyles and Thompson J. Virol. 68:*-**.

The UNG gene is located at the genomic designation UL2 (the second open reading frame of the Unique Long viral segment). See Mullaney. et al. 1989, J. Gen. Virol. 70:449–454.

Production of Herpes Simplex Virus Vectors

HSV-1 is a human neurotropic virus that is capable of infecting virtually all vertebrate cells. Natural infections follow either a lytic, replicative cycle or establish latency, usually in peripheral ganglia, where the DNA is maintained indefinitely in an episomal state.

Replication-competent, recombinant herpes simplex virus vectors of the instant invention contain alterations in expression of two specific herpes simplex virus genes: (1) the gamma 34.5 gene and (2) the uracil DNA glycosylase gene. Such alterations render the product of both genes nonfunctional or reduce their expression such that the mutant herpes simplex virus vector has the properties of the instant invention. Ways to achieve such alterations include (a) any method to disrupt the expression of the product of both of these genes or (b) any method to render the expressed gamma 34.5 gene product and uracil DNA glycosylase nonfunctional.

Numerous methods to disrupt the expression of a gene are known, including the alterations of these genes or their promoter sequences in the HSV-1 genome by insertions, deletions and/or base changes. Roizman and Jenkins. Science 229: 1208 (1985). The mutated herpes simplex virus vector of the instant invention is a replication-competent herpes simplex virus whose genome is altered in the gamma 34.5 gene and the uracil DNA glycosylase gene. Alterations in the gamma 34.5 gene and the uracil DNA glycosylase gene include modifications in either the structural or regulatory sequences of these genes. Genetic alterations can be determined by standard methods such as Southern blot hybridization of restriction endonuclease digested viral DNA, sequencing of mutated regions of viral DNA, presence of reporter gene (for insertions), new restriction endonuclease site, enzymatic assay for uracil DNA glycosylase activity, Western blot or ELISA analysis of infected cell proteins with antibodies to UNG or gamma 34.5, and/or lack of replication in confluent primary cells for gamma 34.5. See Bolovan et al., J. Virol. 68: 48 (1994).

The following genetic manipulations of herpes simplex virus provide examples to illustrate the production of mutant herpes simplex virus vectors. The engineering of the herpes simplex virus vectors of the instant invention exploit two well-characterized genes, the gamma 34.5 and uracil DNA glycosylase genes, in a biologically well-characterized virus.

A herpes simplex virus vector that has been mutated in its gamma 34.5 and uracil DNA glycosylase genes can be isolated after mutagenesis or constructed via recombination between the viral genome and genetically-engineered sequences. The high rate of recombination in herpes simplex virus and the fact that transfected viral DNA is infectious renders genetic manipulation very straightforward. These genetically-altered, replication-competent viruses can be used in the safety and efficacy assays described below.

HSV-1 contains a double-stranded linear DNA genome, 153 kilobases in length, that has been completely sequenced by McGeoch. McGeoch et al., J. Gen. Virol. 69: 1531 (1988). McGeoch et al., Nucleic Acids Res 14: 1727 (1986): McGeoch et al., J. Mol. Biol. 181: 1 (1985); Perry and McGeoch, J. Gen. Virol. 69: 2831 (1988). DNA replication and virion assembly occurs in the nucleus of infected cells. Late in infection, concatemeric viral DNA is cleaved into genomic length molecules that are packaged into virions. In the CNS, herpes simplex virus spreads transneuronally followed by intraaxonal transport to the nucleus, either retrograde or anterograde, where replication occurs.

DNA constructs employing HSV-2 based on those illustrated herein using the HSV-1 genome are encompassed by the present invention. The HSV-2 UNG gene, like the HSV-1 counterpart, is located at UL2 and has been described in several reports; see for e.g., Worrad and Caradonna. 1988. J. Virol. 62:4774–4777. Gamma 34.5 is also present in HSV-2. McGeoch et al., J. Gen. Virol. 72: 3057 (1991).

Impairment of Gene Expression Via Modification of Gamma 34.5 or Uracil DNA Glycosylase Regulatory Sequences Another way to render a herpes simplex virus incapable of expressing functional gamma 34.5 gene product and uracil DNA glycosylase is to impair their expression. The expression of these two genes can be halted by altering the regulatory sequences of the gamma 34.5 and uracil DNA glycosylase genes or by inserting a frame-shift mutation into the nucleotide sequence of the genes.

The regulatory regions for gamma 34.5 and/or uracil DNA glycosylase can be altered by standard techniques to disrupt the expression of the gamma 34.5 and uracil DNA glycosylase gene (UL2). For example, their regulatory sequences could be altered within the viral genome using techniques described above for the alteration of coding sequences.

The promoter region of gamma 34.5 gene has been mapped and the promoter region for uracil DNA glycosylase UL2 has been partly mapped by Singh and Wagner. Virology 196:220–231. The promoter for gamma 34.5 has been mapped to a region within the "a" sequence. The "a" sequence also contains sequences for cleavage of unit length DNA from HSV-1 concatamers, packaging of HSV-1 DNA into capsids and inversion of L and S components, Chou and Roizman, J. Virol. 57: 629 (1986). The promoter region of UNG has been mapped to the extreme left end of thee unique, long HSV-1 region (base pairs 9000–9500 using the sequence numbering of McGeoch) McGeoch et al., J. Gen. Virol. 69:1531–1574.

The effect of these alterations on the regulatory capacity of gamma 34.5 and UNG genes can be detected by insertion of a reporter gene downstream of the promoter. Sze and Herman, Virus Res. 26: 141 (1992). Because herpes simplex virus genes are regulated differently when present in the cellular genome. the effects of each alteration in the gamma 34.5 or uracil DNA glycosylase regulatory component would be assessed in various mammalian target cells. McKnight et al., in CANCER CELLS 4; DNA TUMOR VIRUSES, Cold Spring Harbor (1986) 163–173.

Additional methods for the construction of engineered viruses are known in the art. Additional methods for the genetic manipulation of DNA sequences are known in the art. Generally, these include Ausubel et al., chapter 16 in CURRENT PROTOCOLS IN MOLECULAR BIOLOGY (John Wiley and Sons, Inc.): U.S. Pat. No. 4,603,112, Paoletti et al., issued July 1986. Virological considerations also are reviewed in Coen D. M., "Molecular Genetics of Animal Viruses," in VIROLOGY 123–150 (2nd ed.) (Raven Press, 1990).

The construction of HSV-1 vectors is described, for example, in U.S. Pat. No. 5,288,641; Roizman and Jenkins, J. Science 229: 1208 (1985); Johnson et al., J. Virol. 66: 2952 (1992); Gage et al., J. Virol. 66: 5509 (1992); Spaete and Frenkel, Cell 30; 295 (1982); Goldstein and Weller, J. Virol. 62: 196 (1988), Coen, chapter 7, Virology, Raven Press, 1990; Breakefield and DeLuca, The New Biologist, 3: 203 (1991); Leib and Olivo, BioEssays 15: 547 (1993); Glorioso et al., Seminars in Virology 3: 265 (1992); Chou and Roizman. Proc. Natl. Acad Sci. USA, 89: 3266 (1992); Breakfield et al., Molec. Neurobiol. 1: 339 (1987); Shih et al., in: VACCINES 85, Cold Spring Harbor Press (1985) 177–180; Palella et al., Molec. Cell. Biol. 8: 457 (1988): Matz et al., J. Gen. Virol. 64: 2261 (1983); Mocarski et al., Cell 22: 243 (1980); and Coen et al., Science 234: 53 (1986).

Imparting Hypersensitivity to Antiviral Agents

One safety precaution in the therapeutic use of herpes simplex virus against gliomas involves providing a means to stop any potential infection of other dividing cells. Clinical studies indicate that even wild-type HSV-1 viruses generally do not spread far from the site of initial infection or cause serious systemic disease in immunocompetent individuals. Sacks et al., Ann. Int'l Med. 11: 893 (1989).

Any replication-competent mutant viral vector that is more sensitive to the anti-viral agent than its wild-type parent is deemed hypersensitive to the anti-viral agent, potentially providing a means to prevent an undesired spread of the mutant virus. In constructing herpes simplex virus mutants for use in vivo, the mutants are tested for their sensitivity to current anti-herpetic drug therapies in order to control unforeseen virulent infections. A number of drugs currently are available to treat herpes infections in humans, the most effective being nucleoside analogs that block herpes simplex virus DNA replication. Three herpes simplex virus genes are known to be involved in sensitivity to nucleoside analogs: herpes simplex virus DNA polymerase (UL30, pol), herpes simplex virus thymidine kinase (UL23, tk), and CMV UL97 which shares homology with protein kinases and bacterial phosphotransferases. Furman et al., J. Virol. 32: 77 (1979); Littler et al., Nature 358: 160 (1992); Sullivan et al., Nature 358: 162 (1992).

There are a number of herpes simplex virus DNA polymerase mutants which exhibit hypersensitivity to ganciclovir, including PAAr 5 and AraAr 9. Coen et al., J. Virol. 53: 477 (1985). Unfortunately, intracranial injections of AraAr 9 led to premature death and had no effect on subcutaneous tumor growth. Markert et al., supra. Another mutant herpes simplex virus, the dlsptk virus, is no longer drug sensitive, at least to nucleoside analog drugs, and therefore potentially uncontrollable in vivo.

Attenuation for Neurovirulence

Attenuated or decreased generalized neurovirulence means that life-threatening encephalitis does not ensue after infection with the double mutant herpes simplex virus vector of the instant invention. Because herpes simplex virus-induced encephalitis in humans is very difficult to treat and can be fatal, even with adequate pharmacologic measures, decreased generalized neurovirulence is an important feature of the instant invention. The mutant virus of the present invention is capable of replicating in neoplastic cells but spares surrounding non-neoplastic tissue.

Different herpes simplex virus strains vary in neurovirulence and more attenuated strains may be employed in the construction of the double mutant to further decrease neurovirulence. Other HSV-1 strains available from ATCC include HF (ATCC VR-260), MacIntyre (ATCC VR-539), MP (ATCC VR-735) and HSV-2 strains G (ATCC VR-734) and MS (ATCC VR-540).

Alternatively, any herpes simplex virus gene mutation leading to decreased viral replication in vivo and/or in specific cell populations May be used in the mutated herpes simplex virus vector of the invention. Other neurovirulence genes include but are not limited to: (i) dUTPase [Pyles et al., J. Virol. 66: 6706, (1992)], (ii) UL53 [Moyal et al., Virus Res. 26: 99 (1992)], (iii) alpha 22 [Sears et al., J. Virol. 55: 338 (1985)], (iv) US3 [Meignier et al., Virology 162: 251 (1988)], (v) thymidine kinase gene (UL23/ICP36), and (vi) ribonucleotide reductase (ICP 6).

From a clinical perspective, herpes simplex virus encephalitis is the most commonly reported viral infection of the central nervous system (CNS) in the United States, with an estimated incidence of 2.3 cases per million people. Herpes simplex virus encephalitis is usually localized to the temporal lobe and the limbic system. Histological examination of autopsy cases demonstrates viral antigen at these sites. A number of drugs are available to control infection, including acyclovir 9-92-hydroxyethoxy -methyl)guanine. Zovirax Registered TM, adenine arabinoside (Vidarabine Registered TM ), foscarnet (phosphonoformic acid, PFA) and ganciclovir 9(1,3-dehydroxy-2-propoxy)

methylguanine, DHPG, 2'NDG, Cytovene Registered TM. See Whitley et al., in Lopez et al., (eds.) IMMUNOBIOLOGY AND PROPHYLAXIS OF HUMAN HERPESVIRUS INFECTIONS, page 243 (1990, Plenum Press, N.Y.); Whitley et al., N. Engl. J. Med. 297: 289 (1977); Oberg, Pharmacol. Ther. 19: 387 (1983); DeArmond, Transplant. Proc. 23: 171 (1991).

Achieving Tumor-Specificity

Because herpes simplex virus has a very broad host range and seems capable of infecting all cell types in the CNS, herpes simplex virus mutants of the instant invention may be targeted to specific tumor types using tumor cell-specific promoters. The term "tumor cell-specific promoter" indicates a promoter that is induced selectively or at a higher level in the target tumor cell than in a normal cell. Tumor cell-specific promoters include promoters that are induced selectively or at a higher level in a particular cell type or a tumor cell.

The vectors of the invention also can be designed to selectively replicate in and kill a tumor cell of non-nervous tissue origin. The herpes simplex virus vector of the invention is engineered to place at least one viral protein necessary for viral replication under the control of a cell specific or tumor cell-specific promoter. The tumor cell-specific promoter is induced selectively or at higher levels in tumor cells than in normal cells.

Such tumor cell-specific. HSV-1 and HSV-2 mutants utilize promoters from genes that are highly expressed in the targeted tumor, such as the epidermal growth factor receptor gene promoter (EGFr) or the basic fibroblast growth factor (bFGF) gene promoter or the NESTIN or other tumor associated promoter or enhancer element to drive expression of an essential herpes simplex virus gene (e.g., ICPO or ICP4), under circumstances in which the wild-type essential herpes simplex virus gene would not be expressed. Rendering the essential herpes simplex virus gene non-functional can be achieved by genetic inactivation or replacement of its viral promoter with a tumor cell-specific promoter.

The instant invention encompasses a host-range conditional herpes simplex virus mutant where an essential viral gene product is under the control of a tumor cell-specific promoter rather than its own viral promoter. In permissive cells, containing the proper regulatory proteins for this specific promoter, the essential viral gene product is expressed and the virus is able to replicate and spread to adjacent cells until a non-permissive cell is infected. These studies are applicable to the replication-competent herpes simplex virus of this invention. These constructs, however, are only replication-competent in the correct cell types (i.e., tumor cells) and are replication-deficient in other cells (i.e., surrounding tissue).

Many tumor cell types express phenotypic markers which are turned off in the normal terminally-differentiated cell. One can take advantage of this altered expression pattern to construct tumor cell-specific viruses. Examples of such differentially regulated genes in neural tumors include: (i) nestin, an intermediate filament protein normally expressed in neuroepithelial stem cells, yet not in mature CNS cells, which is ubiquitously expressed in human brain tumors, most prominently in gliomas, (ii) basic fibroblast growth factor (bFGF), a differentiation factor and mitogen for neuroectoderm, which is highly expressed in human gliomas and meningiomas but not in metastatic brain tumors or normal brain tissue and (iii) epidermal growth factor receptor (EGFr), a membrane-bound tyrosine-specific protein kinase that is stimulated by EGF, which is very often overexpressed, altered and the gene amplified in human high grade gliomas but rarely in normal brain.

Herpes Simplex Virus Vectors Effective for Xenogenization

The mutant herpes simplex virus vector of the instant invention can be employed as a genetic therapy against specific tumors by expressing foreign genes in a tumor cell-specific fashion in order to target an immune response that kills the tumor cells. Tepper and Mule, Human Gene Therapy 5: 153 (1994). In addition, the instant invention employs the replication-competent herpes simplex virus vector having decreased neurovirulence as a tumor cell modulator or inducer of an immune response against the tumor cells. The mutant herpes simplex virus vector of the invention can be further altered to express cytokines in the tumor target cell in order to elicit an immune response against the tumor cells. For example, a mutant herpes simplex virus vector can induce viral-mediated killing of tumor cells, which then is amplified by a cytokine-enhanced immune response, a cytokine having been expressed by the vector itself. The expression of cytokines, or other gene products, from the mutant herpes simplex virus vector would occur within hours of infection so that sufficient gene products would be synthesized prior to cell killing. Immune systems-mediated-cell killing may even increase the efficacy of the anti tumor immune response. Barba et al., Proc. Nat'l Acad. Sci. USA 91: 4348 (1994).

Herpes Simplex Virus Vector-Mediated Destruction of Tumor Cells

Exemplary candidates for treatment according to the present invention include, but are not limited to (i) non-human animals suffering from tumors and neoplasms, (ii) humans suffering from tumors and neoplasms, (iii) animals suffering from nervous system tumors and (iv) patients having malignant brain tumor, including astrocytoma, oligodendroglioma, meningioma, neurofibroma, glioblastoma. ependymoma, Schwannoma, neurofibrosarcoma, and medulloblastoma.

Preferentially, the treatment will be initiated by direct intraneoplastic inoculation. For tumors in the brain, MRI, CT, or other imaging guided stereotactic technique will be used to direct viral inoculation or virus will be inoculated at the time of craniotomy.

The pharmaceutical compositions of the present invention would be advantageously administered in the form of injectable compositions. A typical composition for such purpose would comprise a pharmaceutically acceptable vehicle. For instance, the composition could contain human serum albumin in a phosphate buffer containing NaCl. Other pharmaceutically acceptable carriers include aqueous solutions, non-toxic excipients, including salts, preservatives, buffers and the like. See REMINGTON'S PHARMACEUTICAL SCIENCES (15th ed.) 1405–1412 & 1461–1487, Mack Publishing Co. (1975), and THE NATIONAL FORMULARY XIV (14th ed.), American Pharmaceutical Association (1975). Examples of non-aqueous solvents are propylene glycol, polyethylene glycol, vegetable oil and injectable organic esters such as ethyloleate. Aqueous carriers include water, aqueous solutions saline solutions, parenteral vehicles such as sodium chloride. Ringer's dextrose, etc. Intravenous vehicles include fluid and nutrient replenishers. The pH and exact concentration of the various components of the pharmaceutical composition are adjusted according to routine skills in the art, Goodman and Gilman. THE PHARMACOLOGICAL BASIS FOR THERAPEUTICS (7th ed.).

Typically, the herpes simplex, virus vector would be prepared as injectables, either as liquid solutions or suspensions: solid forms suitable for solution in, or suspension in liquid prior to injection may also be prepared. The preparation also may be emulsified. The active immunogenic ingredient is often mixed with an excipient which is pharmaceutically-acceptable and compatible with the active indent. Suitable excipients are, for example, water, saline, dextrose, glycerol, ethanol, or the like and combinations thereof. In addition, if desired, the vector may contain minor amounts of auxiliary substances such as wetting or emulsifying agents, pH-buffering agents, adjuvants or immunopotentiators which enhance the effectiveness of the vector vaccine.

Additional formulations which are suitable for other modes of administration include oral formulations. Oral formulations include such typical excipients as, for example; pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders and contain 10%–95% of active ingredient, preferably 25–70%.

The composition can comprise, in addition to a virus, compounds and/or compositions that will also aid in treating the tumors or the accompanying symptoms, such as, radioactive seed implants, antibiotics, growth factors (e.g., GMCSF or erythropoietin), other forms of genetic therapy, including but not limited to, retroviral and adenoviral vector systems and immunomodulating therapies such as IL-2, IL-12 or others as they are deemed appropriate. In addition, the mutant replication-competent HSV strain may be administered with other pharmaceuticals that will be used at the clinicians discretion to treat post-operative symptoms, including but not limited to, anti-convulsants, sedatives, steroids and immunomodulating chemicals. Dosages for the above-mentioned additional compounds are established and known to those skilled in the art. The viral therapy may also be given in conjunction with general raiotherapy and/or general chemotherapy.

The compounds useful in the present inventive method may be administered by any suitable means. One skilled in the art will appreciate that many suitable methods of administering the compound to an animal in the context of the present invention, in particular a human, are available, and, although more than one route may be used to administer a particular compound, a particular route of administration may provide a more immediate and more effective reaction than another route.

The term "unit dose" refers to physically discrete units suitable for use in humans, each unit containing a predetermined quantity of active material calculated to produce the desired therapeutic effect in association with the required diluent, i.e., carrier or vehicle, and a particular treatment regimen. The quantity to be administered both according to number of treatments and amount, depends on the subject to be treated, capacity of the subject's immune system to synthesize antibodies; and degree of protection desired. Precise amounts of active ingredient required to be administered depend on the judgment of the practitioner and are peculiar to each individual. However, suitable dosage ranges are on the order of one to several hundred micrograms of active ingredient per individual. Suitable regimes for initial administration and booster shots also vary but are typified by an initial administration followed in one or two week intervals by one or more subsequent injections or other administration.

Treatment of Human Brain Tumors with Replication-competent Viral Vector

Patients with recurrent glioblastoma that was refractory to standard surgery radiotherapy and chemotherapy would be treated with herpes simplex virus therapy. The patient would be scanned using MRI or CT or other technique and the tumor and normal brain registered in stereotactic space. The virus would be administered using stereotactically guided neurosurgical techniques. A computer tomography (CT) scan or magnetic resonance imaging (MRI) scan computes the stereotactic frame that would be used to accurately inoculate virus into a tumor at one or more locations. Virus would be inoculated at a dose of about $10^1$ to about $10^7$ p.f.u. per inoculation using a <2 mm cannula. The number of sites inoculated would depend on the size of the tumor. Patients would be followed with periodic MRI scans and with neurological examination, blood count, and liver function tests.

In an alternate scheme, craniotomies will be performed for total gross tumor ressection in with recurrent tumor and virus will inoculated in the resected tumor bed in a fashion similar to above.

Replication-competent Herpes Simplex Virus Vector Vaccines

The herpes simplex virus vector of the invention can be used as a vaccine to protect an animal against herpes simplex virus infection. In the present context, "protecting" a subject against herpes simplex virus includes both (1) a prophylactic vaccine, i.e., a vaccine used to prevent a future herpes simplex virus infection, and (2) a therapeutic vaccine for treating an existing herpes simplex vital infection. The herpes simplex virus sample would be prepared using standard methodology. Herpes simplex virus-infected Vero cells would be frozen at −70° C. until they are to be used. The material would be thawed and the cell debris would be pelleted by centrifugation. The supernatant fluid would be discarded and the pellet resuspended to its original volume. This material would most closely approximate that used in vaccine manufacture. This suspension would be sonicated three times for 30 seconds.

Herpes simplex virus plaque titers would be determined by standard procedures. For example, the virus would be titrated in triplicate on monolayers of Vero cells in 6-well plates. After adsorption of samples for 2 hours, cells would be overlayed with media containing 0.6% agarose and incubated at 37° C. in a $CO_2$-rich environment for 48 h. A second overlay, the same as above except for addition of neutral red, would be added and the cells would be incubated an additional 24 hours.

The herpes simplex virus pools would be titrated before filtration. The pools then would be filtered through a Nalgene 0.45 mu m filter sampled refiltered through a second filter and then resampled.

EXAMPLES

The following examples are provided by way of illustration and are not intended to limit the scope of the invention, which is determined by the claims.

Construction and Characterization of an Oncolytic or Vaccine HSV Double Mutant

Materials and Methods

Cells and Viruses

African Green Monkey kidney cells (VERO; CRL 1586), the human glioblastoma cell line, U87MG (HTB 14), and the human breast carcinoma cell line MDA-MB-231 (HTB 26) were obtained from the ATCC (Rockville, Md.). VERO and U87MG cells were cultured as recommended by the ATCC. MDA-MB-231 cells were cultured in MEM-a medium supplemented with 10% FBS, 100 units/ml of penicillin G, and 100 mg/ml of streptomycin (MED medium). The human medulloblastoma cell line DAOY was obtained from Dr. Walter Hall (Univ. of Minn.; Wen et al., 1995) and cultured in MED medium and passaged once every four days. The human neuroblastoma cell lines N (neurite-bearing) and S (substrate-adherent) were cultured as previously described (Foley et al., 1991). A clonal derivative of the human hemangiosarcoma cell line. SKBR3 (Heffelfinger et al., 1992), was isolated by Dr. Susan Heffelfinger (Univ. of Cincinnati) and was designated SK-M. SK-M cells also were grown in MED medium and passaged once every four days. The SK-M cell line is of endothelial origin. Cell culture supplies were purchased from GIBCO/BRL (Gaithersberg. MD). All cells were maintained in a 37° C., 5% $CO_2$-humidified environment.

For studies of viral replication in a non-dividing cell population. embryonic rat dorsal root ganglion cultures were kindly provided by Dr. Nancy Ratner (Univ. of Cincinnati). These cultures were prepared from dorsal root ganglia harvested from day E15 rat embryos (Oncogene 11, 35–335.) and then, following plating at a density of ~2000 cells/collagen-coated coverslip, the cells were cultured for two weeks first in medium to kill active cells (Dulbeccos modified essential medium supplemented with 10% human plasma serum nerve growth factor and fUdR at 0.5%) and then in the same medium without the fUdR.

The virus strains used in these studies were derived originally from the wild type HSV-1 strain F. Strain F was chosen for this work because it has reduced neurovirulence as compared to other laboratory isolates of wild type HSV-1 (Infect. Immun. 40, 103–112.). Both strain F and its derivative ICP34.5 deletion mutant, R3616 (Science 250, 1262–1266.) were kindly provided by Dr. B. Roizman (Univ. of Chicago).

Virus stocks were prepared from subconfluent VERO cell monolayers that had been infected 48 hours prior to harvesting. The virus was concentrated from sonicates of infected cells And then titered using standard methods. All virus stocks were stored at –80° C. in VERO culture media. HSV-1 genomic DNA for transfection and for restriction endonuclease analyses was prepared as described (J. Virol. 68, 4963–4972.).

Generation of the 3616UB Virus Strain

To generate 3616UB, the HSV-1 UNG open reading frame (ORF; UL2, bps 9886–10888) of R3616 was disrupted as the result of recombination of R3616 with a plasmid that contains the E. coli b-galactosidase (LacZ) gene under the control of the SV40 early promoter inserted into the unique Xba I site within the cloned UNG ORF (J. Virol. 68, 4963–4972.). Genomic R3616 DNA and the UNG mutant plasmid DNA were cotransfected into VERO cells with Lipofectase (GIBCO/BRL). This strategy was used previously to mutate the UNG gene of HSV-1 strain 17 syn$^+$ (J. Gen. Virol. 70, 449–454; J. Virol. 68, 4963–4972.) This mutation strategy was used to examine the contribution of HSV-1 UNG Activity to viral mutation frequencies and in that study was found to be extremely stable with no loss of the LacZ insert in almost 1000 plaques examined (J. Virol. 68, 4514–4524.). Base pair numbering, restriction endonuclease fragment names and maps are based upon the complete sequence of HSV-1 strain, 17 syn$^+$ compiled by McGeoch and colleagues (J. Gen. Virol. 69, 1531–1574.). Recombinant viruses were identified by the formation of a blue precipitate following incubation with the chromogen X-Gal (5-bromo-4-chloro-3-indolyl-b-D-galactopyranoside: GIBCO/BRL). LacZ-expressing "blue" plaques were purified to homogeneity by limiting dilution.

The genomic structure of the 3616UB virus was confirmed by Southern blot, RFLP analysis. Briefly, viral genomic DNA that had been digested with appropriate restriction enzymes was size-separated in 1% agarose and blotted onto Biodyne-B membrane (GIBCO/BRL). The blots were hybridized to $^{32}$P-labeled probes specific for the UNG, LacZ or ICP34.5 genes at 42° C for 24 hours. Following washing, the blots were exposed to XOMAT-AR films (Eastman Kodak: Rochester, N.Y.) for 6–24 hours.

Animal Studies

Four to five week old (20–22 gm), female. CB 17 severe combined immunodeficient (SCID) or outbred Swiss Webster mice (Charles River Breeders) were used throughout these studies. Animals were housed in microisolator cages in American Association for Laboratory Animal Care-approved quarters and provided with unlimited access to food and water. Animals were quarantined for 7 days prior to any procedures.

Neurovirulence, or the capacity of the virus to replicate in murine brain, as indicated by development of fatal encephalitis, was quantified by PFU/lethal dose 50% (PFU/$LD_{50}$) ratios following freehand, percutaneous intracranial inoculation of 10-fold serial dilutions of strain F (positive control), or the novel strain 3616UB. Groups of 6 mice were injected following Metofane anesthesia, in the left brain hemisphere, monitored for 21 days and scored for death. PFU/$LD_{50}$ ratios were calculated using the method of endpoint estimation as described by Reed and Muench (Amer. J. Hyg. 27, 493–497). To directly assess viral replication in healthy brain tissues. CB 17 SCID mice were stereotactically injected with either HSV-1 strain F or 3616UB in the right frontal lobe. A volume of 10 ml that contained 1×10$^8$ PFU/ML of virus was delivered over a 15 min. period. At 24 or 48 hours post injection, animals then were sacrificed and the injected brain hemisphere examined for HSV-1 antigen by immunohistochemistry with a polyclonal HSV-1 antiserum (Accurate Chemical and Scientific Corp.; Westbury, N.Y.).

Tumor xenografts were produced by flank injection of DAOY or SK-M cells that had been cultured to confluency and then harvested by trypsinization into culture media. Cell density was adjusted to ~10$^6$ cells/125ml of culture media for flank injections. For each injection site, 125 ml of cell suspension was mixed with an equal volume of Matrigel (Collaborative Research, Inc.) to enhance tumor xenograft formation prior to injection. For all experiments, tumor cells were injected subcutaneously into both rear flanks of anesthetized animals.

Intratumoral injections of viral stock were performed when the xenografts reached a volume of 50 or 100 mm$^3$ (a diameter of 5–10 mm). For each xenograft. an injection of 30 ml that contained 3×10$^6$ PFU of 3616UB or R3616 was performed, delivering the virus to the approximate center of the tumor. For the therapy studies, groups of 10 tumors were injected with 3×10$^6$ PFU of 3616UBI or R3616 or an equivalent amount of medium alone. An identical second injection was given 7 days after the first. Tumor growth ratios were established from tumor volumes that were calculated using the formula length×width$^2$/2.

In situ Localization of Viral Antigen

Viral antigens in tumor xenografts or healthy brain tissue were detected by immunofluoresence (Cancer Res. 51, 6338–6345.). For immunofluoresence studies, paraffin-embedded tissue sections were mounted on Plus slides (Fisher). Following paraffin clearing and rehydration, the sections were rinsed in phosphate-buffered saline and then were blocked with 5% non-fat dry milk in tris-buffered saline, pH 7.4 (TS) for 40 min. Viral antigens present in infected cultured cells were detected following fixation with 4% paraformaldehyde for 10 min. at room temperature. A polyclonal antiserum to HSV-1 diluted 1:100 in 5% milk/TS was applied to the tissue or cell monolayer and incubated overnight at 4° C. Following extensive rinsing in TS, goat anti-rabbit-FITC (Kirkegaard and Perry), was applied at a dilution of 1:50 in 5% milk/TS and incubated at room temperature for 1 h. Following rinsing, the specimens were mounted with polyvinyl alcohol containing 0.1% 1,4-diazabicyclo(2.2.2)octane (DABCO; HARLOW, E., and LANE. D. (1988). Antibodies: A laboratory maual. p. 418. Cold Spring Harbor Laboratory, Cold Spring Harbor, N.Y.). A monoclonal antibody to the intermediate filament protein vimentin (DAKO, Carpinteria, Calif.) was used in some experiments to visualize noninfected cells because it efficiently labeled each of the selected tumor cell lines. In all experiments, tissue specimens were incubated with secondary antibody alone as a negative control. Photomicrographs were generated on a Zeiss Axiophot using TMAX 100 film (Eastman/Kodak).

In Vitro Cell Killing

To assay the killing efficiency of HSV-1 strains in vitro. each tumor cell type was cultured to confluency and then infected at a multiplicity of infection (MOI) of either 0.0001, 0.01 or 1. For each experiment, at least 2 cultures were infected in parallel. Strains F and R3616 served as positive controls for cell monolayer infection because both strains previously have been shown to replicate in a number of the cell lines we examined (Science 252, 854–856: Nature Med. 1. 938–943.). Infected monolayers were observed at 12 hour intervals and scored for cytopathic effect (CPE) as a percentage of the monolayer showing evidence of herpetic infection. To confirm that the monolayers were dying as a result of herpetic infection, parallel cultures were fixed with absolute methanol at –20° C. at 24 hour time points and then immunostained for HSV-1 antigen as described in the previous section. For these experiments, mock-infected cultures served as negative controls for both CPE and HSV-1 antigen production.

Ganciclovir Sensitivity

To test the sensitivity of the HSV-1 strains to ganciclovir (GCV), monolayers of DAOY or VERO cells were infected with 3616UB, R3616 or F at an MOI of 0.01 and then triplicate cultures were incubated with medium alone or in medium supplemented with 75 ng/ml GCV. After 48 hours, the infected monolayers were harvested and viral titers determined. The titers attained by each viral strain were established in triplicate wells, averaged and used to establish standard deviations. The average values then were compared under the two different conditions to establish the sensitivity to GCV as the percent of plaque reduction.

To further characterize the GCV sensitivity of 3616UB, duplicate monolayers of DAOY or VERO cells infected with 100 PFU of either 3616UB, R3616 or F were exposed to medium alone (control) or increasing doses of GCV. After 48 hours of culture in the presence of 0.03% human gamma globulin (Gammar) to control secondary plaque formation, plaques were counted in crystal violet-stained monolayers. The mean number of plaques at each dose of GCV was divided by the mean number of plaques in the GCV-free cultures, and multiplied by 100, to obtain a percent plaque inhibition by GCV. The data were then plotted to extrapolate an inhibitory dose 50% ($ID_{50}$) of GCV for each virus in both DAOY and VERO cells. Statistical analyses were completed using one way analysis of the variable (ANOVA) tests and GraphPad Instat software.

Results

Generation of 3616UB

Figure 1B:
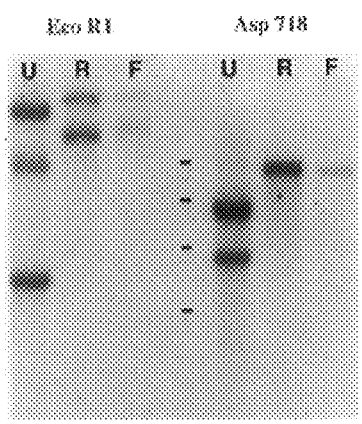
Figure 1C:
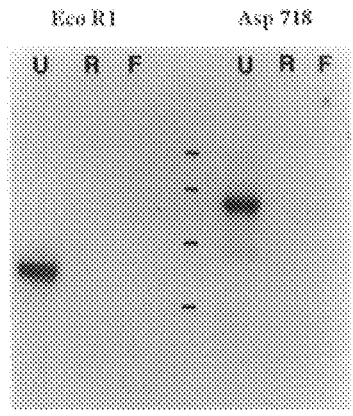

To generate the viral multiple-mutant, 3616UB the UNG ORF (bps 9886–10888) in R3616 was disrupted by insertion of a ~4 kb Xba I fragment containing the LacZ gene under the control of the SV40 promoter (FIG. 1A depicts this strategy). Southern blot analyses indicated that the genomic structure of 3616UB was as expected at the UNG and 34.5 gene loci (FIG. 1, and data not shown). Blots of genomic DNA digested with either Eco R1 or Asp 718 and hybridized to either a probe specific for the UNG locus (HSV bps 8662–11820; panel B), or a LacZ probe (panel C) showed that 3616UB DNA (lanes 1 & 4), relative to strain F or genomic parent R3616 DNA (lanes 3 & 6 and 2 & 5, respectively), contained the expected new Eco R1 and Asp 718 sites, as well as an additional 4 kB in the UNG locus, reflecting the insertion of the LacZ gene in that region. The UNG probe hybridized to a single 12.610 bp Asp 718 fragment in strain F and R3616 lanes (panel B), because the wild type UNG locus does not contain an Asp 718 site (see panel A), and to two bands totaling approximately 16.600 bp in 3616UB. The LacZ insertional event at the UNG locus was confirmed by the comparison of Eco R1 digestion of the DNA of the three viral strains. The LacZ-specific probe hybridized to bands of expected size following digestion with either Eco R1 or Asp 718 (panel C). These bands are not present in either the R3616 or strain F lanes. Finally, to verify that 3616UB contained the ICP34.5 deletion of its parent virus, R3616, Southern blots of the digested viral DNAs were hybridized to a probe for the ICP34.5 locus, in which the 1 kb deletion was observed in both 3616UB and R3616 DNAs (data not shown). Together, these findings support the predicted structure of the engineered 3616UB strain.

To assess whether the LacZ reporter gene in 3616UB was functional, cell cultures that had been infected with 3616UB were fixed after 24 hours and then stained with the chromagenic substrate for b-galactosidase. Blue staining was detected in all viral plaques, indicating a correlation between herpes infection and LacZ expression. The b-gal activity was located at the plaque margin only, suggesting that LacZ expression from 3616UB provides an indicator of the initial infection of cells (FIG. 3D). This data indicates that the LacZ gene is functional, allowing for the histochemical localization of the 3616UB-infected cells. Staining of infected monolayers with X-gal also showed that the UNG gene mutation was stable because no LacZ negative plaques (potential UNG revertants) were observed in over 5000 that were examined (data not shown).

Strain 3616UB generated titers in VERO monolayers that were equivalent to that of its parent strain R3616 and its grandparent strain F. In each of the cultured cell types examined strain 3616UB effectively replicated to titers of ~$10^8$ PFU/ml with the same relative kinetics as the wild type grandparental strain F (data not shown).

Ganciclovir Sensitivity

Figure 2A:
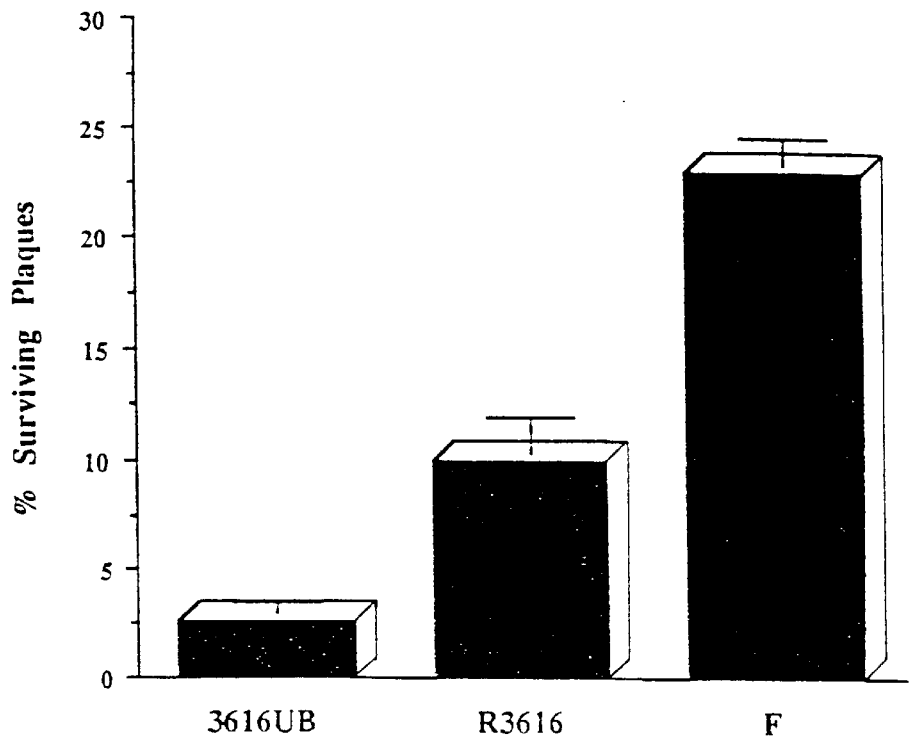

Because strain 3616UB is to be used as a human tumor therapy, it was necessary to establish that the therapy can be controlled using chemical intervention. To determine whether 3616UB retained sensitivity to antiherpetic drugs, we examined the effect of ganciclovir (GCV) on 3616UB-infected cultured cells. Unexpectedly, 3616UB was found, by 2 independent assays, to be significantly more sensitive to GCV than either the direct parental strain R3616 or the wild type strain F (ANOVA, $p \leq 0.01$). Cultures of VERO cells infected with either 3616UB, R3616, or F that were treated with 75 ng/ml of GCV generated less virus than control cultures infected in parallel, but not exposed to GCV. By comparing the percent of plaques that still formed following exposure to this concentration of GCV, 3616UB was identified as the most sensitive to GCV among the three strains (2.59±0.4% for 3616UB vs. 9.85±1.6% and 22.85±1.2% for R3616 and F, respectively; FIG. 2A). These findings were equivalent to the results from similar experiments performed in DAOY monolayers (data not shown).

Figure 2B:
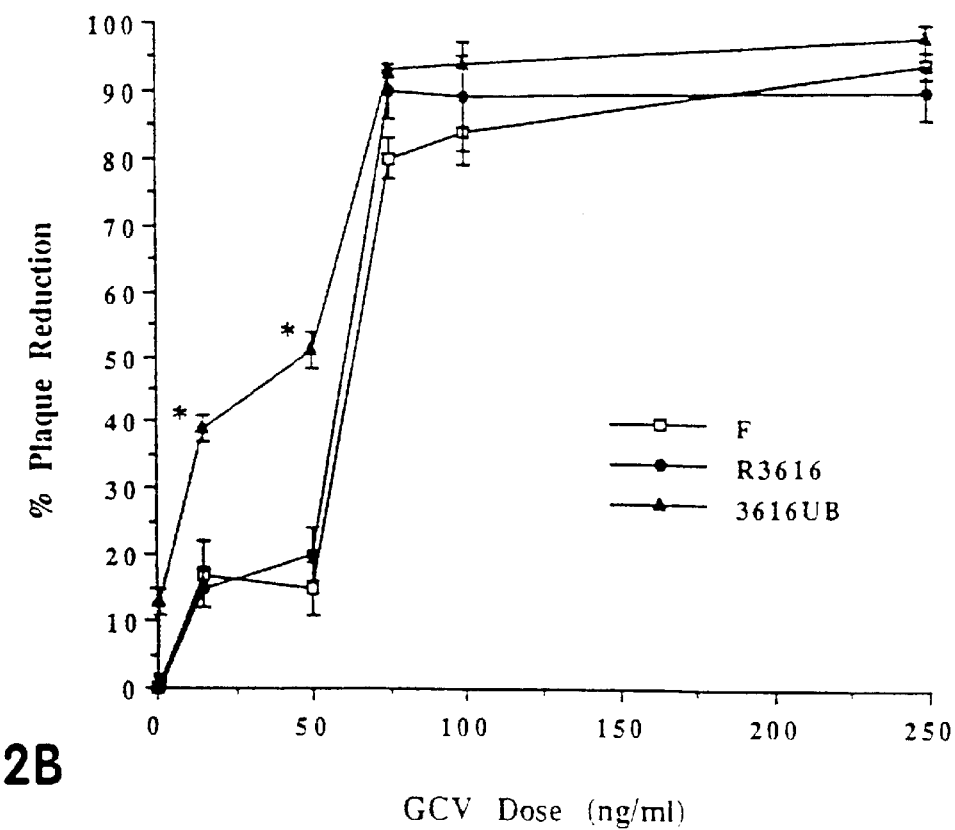

Consistent with the single dose study, a GCV dose response analysis showed that a much lower dose of GCV was required to reduce the titer of 3616UB than was required to inhibit strain R3616 or F. The dose of GCV that reduced the number of 3616UB plaques by 50% ($ID_{50}$) was extrapolated from the plotted plaque-reduction assay data and was found to be 50 ng/ml. The $ID_{50}$ for strain R3616 and strain F in this study was ~80 ng/ml. Significant reductions in 3616UB titers as compared to strain F titers were observed at GCV doses of 15, 50 and 100 ng/ml (ANOVA $p \leq 0.01$); at this same GCV concentration R3616 and F were only minimally inhibited (FIG. 2B).

In Vitro Cytopathic Effect in Cultured Cells

Figure 3A:
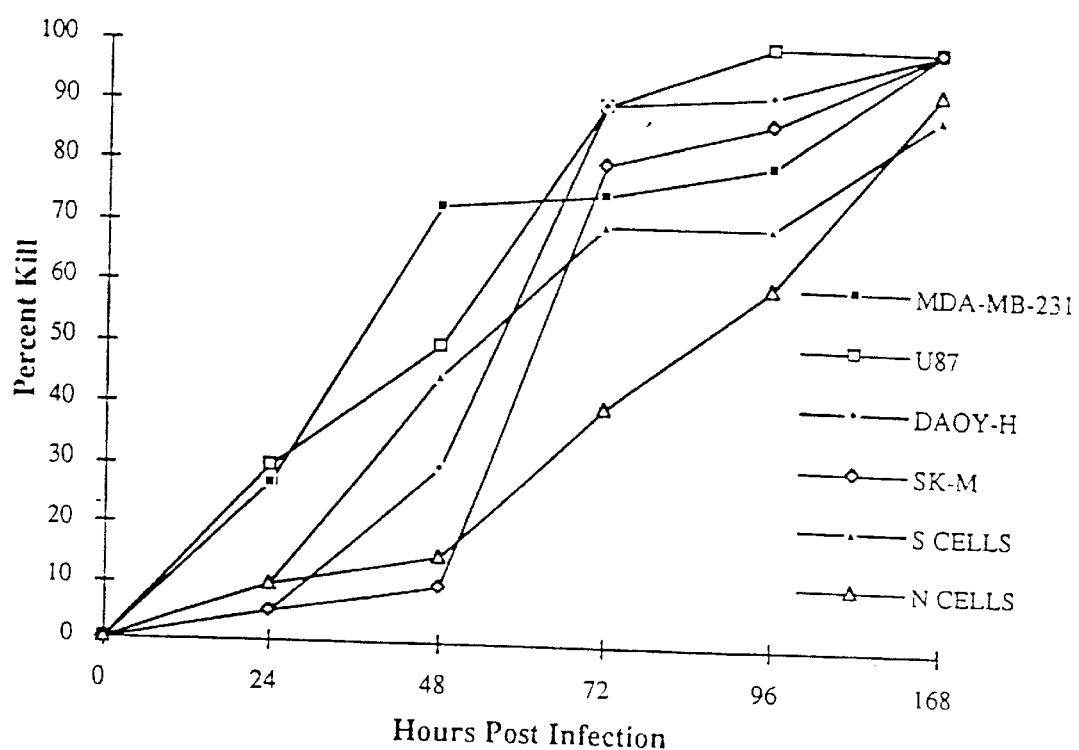

To test that 3616UB would be an effective cytolytic agent for brain tumor cells, we determined whether this virus retained the ability to replicate in, spread through and destroy a cultures monolayer of human tumor cells. Using CPE as an outcome, we examined the results of 3616UB infection of 6 different cell lines including three human cancers that originate in, or commonly metastasize to the brain. To more closely model an in vivo situation, where the number of tumor cells would far exceed the number of injected viral particles, a low multiplicity of infection (MOI of 0.0001) of the monolayers was performed. In every cell line examined, including DAOY (medulloblastoma), U87MG (glioblastoma), N and S cells (neuroblastoma), SK-M (hemangiosarcoma), and MDA-MB-231 (breast carcinoma), 3616UB was found to destroy the monolayer within 5 days (FIG. 3A). As expected, mock-infected control cultures showed no cytopathic effect. The immunolocalization of HSV antigen in the cultures exposed to 3616UB confirmed that 3616UB was replicating in the tumor cells in vitro (FIG. 3B, C & D show the infection of DAOY cells as an example). Viral infection of DAOY cells (see FIG. 3B) was evident as soon as 24 hours after infection with as little virus as 1 3616UB PFU per 10,000 cells. Further evidence of 3616UB infection in DAOY was illustrated by staining with X-gal (FIG. 3D) at 24 hours after infection.

Figure 4A:
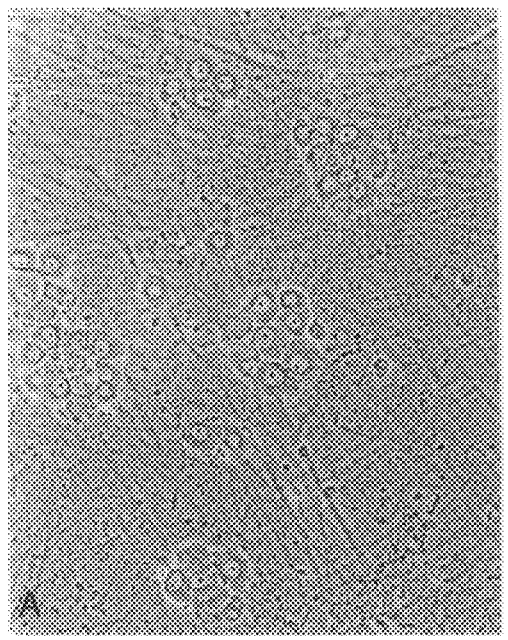
Figure 4B:
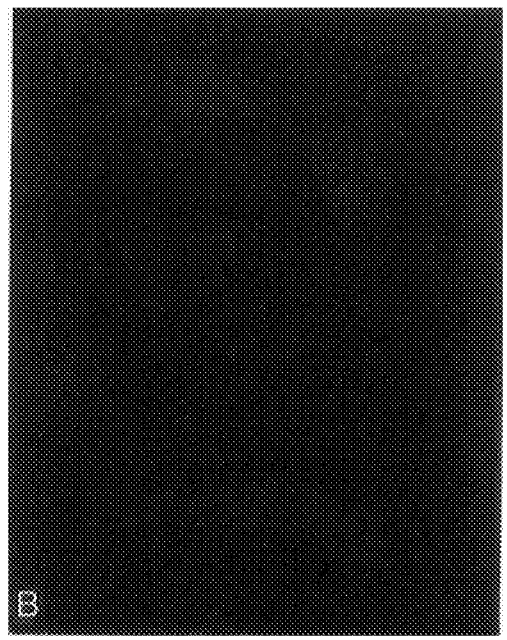

The mutations engineered in 3616UB were chosen to prevent this strain from replicating in and killing nondividing cells near the tumor. To determine whether 3616UB replicated in a non-dividing cell population, primary embryonic rat dorsal root ganglionic neuron cultures were infected at MOIs of 0.001, 1 or 10 with each of the three viral strains. Even 7 days after infection with an MOI of 10, 3616UB did not adversely affect the neuronal cultures. The observation that 3616UB did not replicate in these cultures was confirmed by the lack of immunostaining for HSV-1 antigens and the lack of virally-induced CPE (FIG. 4A & B). As a more quantitative measure of viral replication, duplicate neuronal cultures were harvested at 7 days post infection, sonicated to release infectious virus and then titered on VERO cells. By this measure, 3616UB did not produce any detectable progeny, even at the highest MOI (Table 1).

TABLE 1

Virus generated by replication in rat primary neuronal cultures.

| | HSV-1 STRAIN | | |
|---|---|---|---|
| MOI | 3616UB | R3616 | F |
| 10 | none detected | 10 PFU/ml | $2 \times 10^5$ PFU/ml |
| 1 | none detected | none detected | $1 \times 10^5$ PFU/ml |
| 0.01 | none detected | none detected | $6 \times 10^3$ PFU/ml |

Figure 4C:
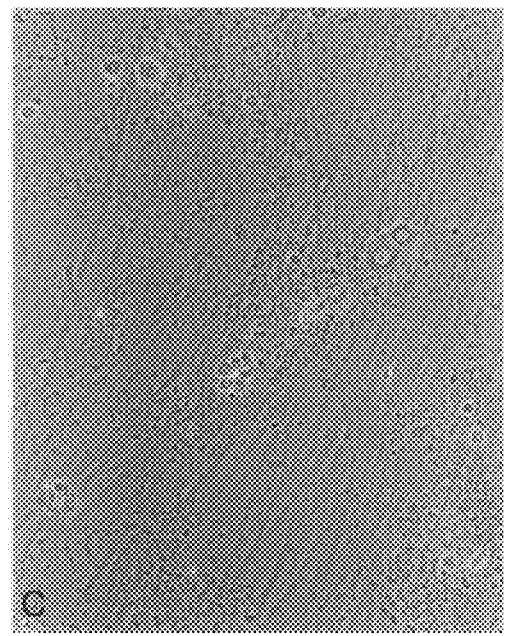
Figure 4D:

In contrast, strain F replicated in and eventually led to the destruction of the neuronal cultures at all three MOIs within the 7 day observation period. Strain F generated titers as high as $10^5$ PFU/ml following infection at MOI of 1 or 10 (Table 1) and led to the production of robust levels of HSV antigen as detected by immunohistochemistry (FIG. 4C). Unexpectedly, 3616UB's parental strain, R3616, was found to replicate in and produce a small amount of progeny virus after infection of neuronal cultures with high doses of virus (Table 1: MOI of 10). The R3616 virus detected at 7 days post infection could only represent virus produced from active replication in the neuronal culture. In the neuronal cultures infected with 10 R3616 PFU/cell. HSV-1 antigens were immunolocalized to no more than 1% of the total neurons suggesting limited replication of this virus (data not shown).

Tumor Xenograft Infection by 3616UB

Although 3616UB was found to efficiently infect and spread through cultured monolayers of human tumor cell lines, in vitro tests can not completely predict in vivo efficacy. Therefore, to determine if 3616UB could infect and spread through a tumor, we established flank xenografts of a human tumor cell line that was destroyed completely by 3616UB in vitro. Tumors of the medulloblastoma line DAOY in CB17 SCID mice were observed until they attained volumes of at least 100 mm³. Then, 30 ml of a $1 \times 10^8$ PFU/ml stock of 3616UB was delivered at a single site within the tumor. Mice were sacrificed at 12, 24, 48 or 72 hours after 3616UB injection and the tumors were harvested and excised from surrounding mouse tissues and then processed for immunohistochemistry with antibody to HSV-1.

Figure 5A:
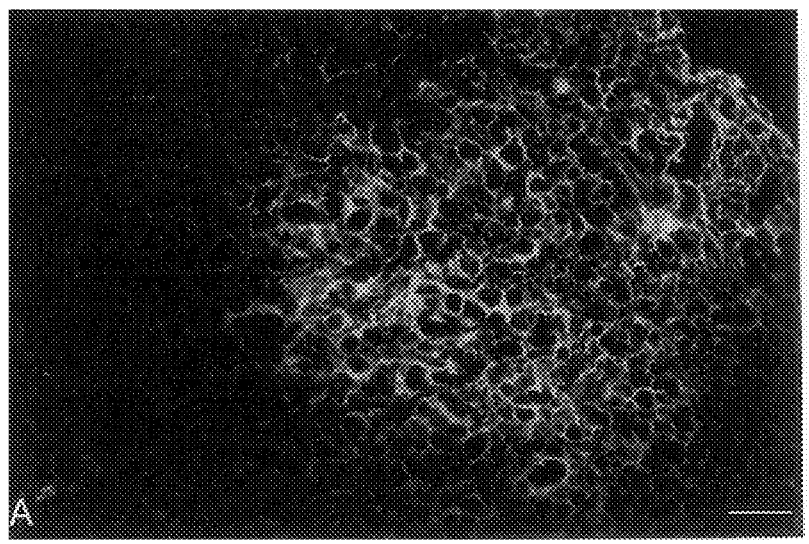
Figure 5B:
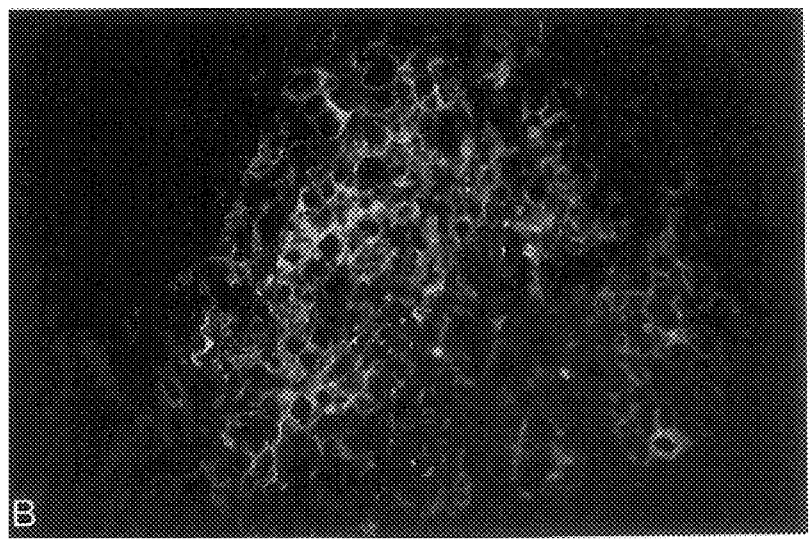

As early as 12 hours after injection, 3616UB infection at the site of injection was evident by HSV-1 antibody labeling of tumor cells (a representative DAOY tumor section is presented in FIG. 5A). By 48 hours after 3616UB treatment, tumor cells distant to the site of injection also were infected (FIG. 5B). Unexpectedly, considerably less HSV-1 antigens were detected at 72 hours post 3616UB treatment (data not shown). By qualitative examination of each time point, the largest number of labeled foci in 3616UB-infected tumors were detected at 48 hours after infection. Mock-infected xenografts were not labeled by the HSV-1 antibody (data not shown). Based on the presence of substantial amounts of HSV-1 proteins in large foci near the injection site and at sites distant from the injection, 3616UB is capable of infecting and spreading through human medulloblastoma xenografts.

The therapeutic value of 3616UB was examined by injection of 30 ml of $1 \times 10^8$ PFU/ml intratumorally into 10 tumors of 50 mm³ volume previously established in the flanks of SCID mice. Additional groups of 10 tumors were injected with either R3616 or medium alone for comparison and control, respectively. Tumor models of medulloblastoma using slow-growing DAOY cells, and hemangiosarcoma, a faster-growing tumor type that occasionally metastasizes to the brain (Folia Neuropath. 33, 215–220.), utilizing SK-M cells, were studied. Upon completion of the treatment, tumor volumes were calculated from measurements of the tumor mass and were used for the determination of growth ratios (FIG. 6).

Figure 6A:
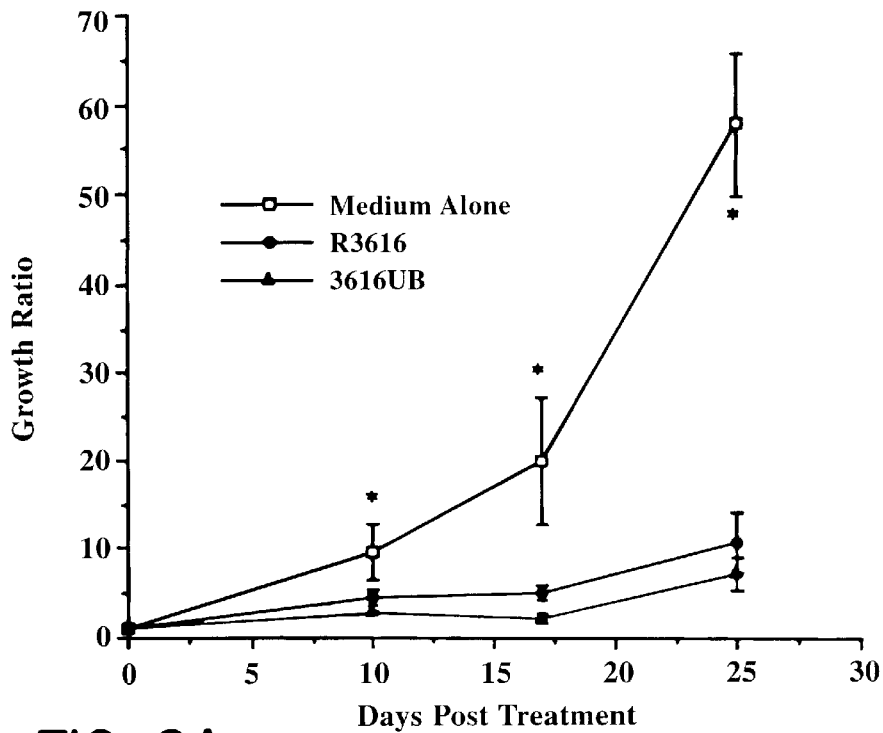
Figure 6B:
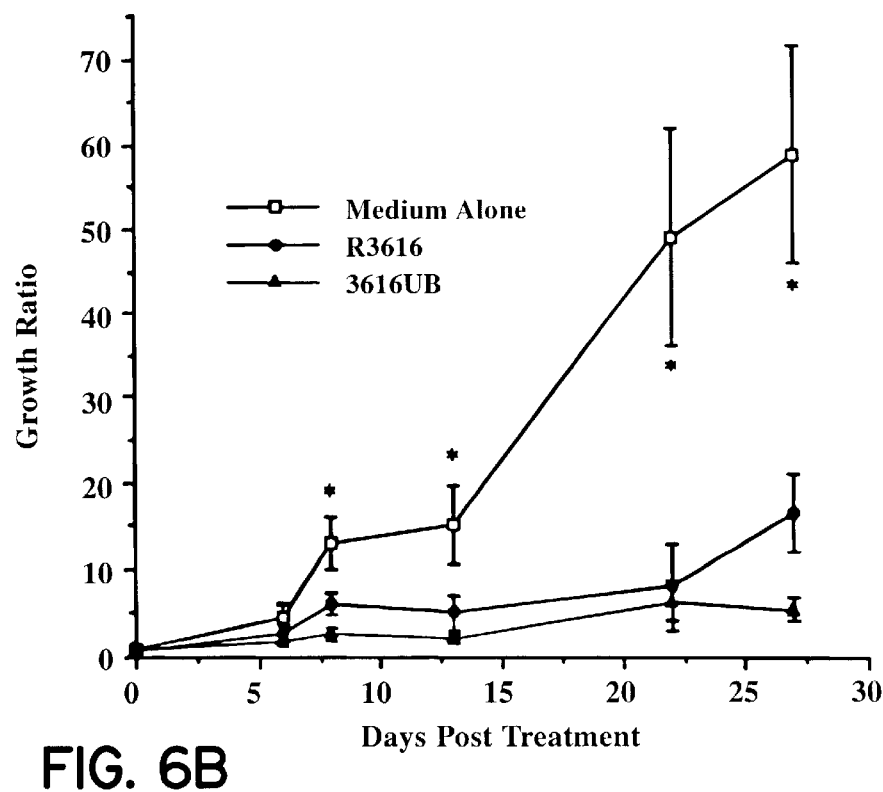

By 10 days after completion of treatment, significant growth arrest of tumors was evident in groups treated with either 3616UB or R3616 when compared to the medium alone-treated tumors (p<0.01 by ANOVA analysis; FIG. 6A and 6B). In several animals, full regressions were noted with no palpable tumor present. In all cases of regression, upon cessation of herpes treatment, tumor masses emerged before the end of the study, suggesting a strong suppressive effect of herpes on tumor growth and the possible usefulness of multiple application of the herpes therapy.

Toxicity Assessment of 3616UB

Having established the therapeutic potential of 3616UB, we sought to determine whether this strain caused any neurotoxicity in murine models. Previous studies on R3616, the parent strain of 3616UB, showed that R3616 was significantly neuroattenuated like an analogous ICP34.5 mutant generated in a different HSV-1 wild type background (J. Gen. Virol. 73, 967–970: J. Gen. Virol. 75, 2059–2063). Although it was unlikely that mutation of the UNG gene in R3616 would have increased its neurotoxicity, we examined whether 3616UB infected and/or caused disease in healthy murine brain tissues. Intracranial injection of 10-fold dilutions of virus in groups of 6 Swiss Webster mice was performed in order to establish a PFU/lethal dose 50% ($PFU/LD_{50}$) ratio. The toxicity of 3616UB was studied in an immunocompetent mouse to determine if the significant HSV-1 antigen load that would be delivered in a therapeutic dose of 3616UB caused immunological damage to healthy tissue near the site of injection. As predicted, infection with 3616UB did not cause any neurological symptoms or fatal encephalitis in any of the mice injected with the highest titers attainable ($1 \times 10^8$ PFU/ML: Table 2). R3616, the parent of 3616UB, resulted in the death of 1/6 animals following direct intracranial injection of high titer stock, but in the majority of mice did not cause any signs of neurological distress. The wild type strain F generated a $PFU/LD_{50}$ ratio of $5 \times 10^4$ (Table 2).

A second set of toxicity experiments was performed in SCID mice to rigorously test the potential for disease associated with application of high doses of 3616UB in animals that are more sensitive to herpetic infection than are Swiss Webster mice (Archives of Virol. 103, 73–82.). Neither strain 3616UB nor R3616 were found to cause any signs of neurological disease in SCID mice following direct intracranial injection (Table 2). As in the immunocompetent animals, high titers of strain F in SCID mice led to the development of fatal encephalitis in 100% of the animals studied.

Figure 7A:
Figure 7B:

To determine if replication of 3616UB was occurring in healthy brain tissue we examined by immunohistochemistry the tissue surrounding the injection for evidence of production of HSV-1 proteins. HSV-1 protein was not detected in brain sections at or near the needle track at the 24 or 48 hour time point in any of the mice (FIG. 7A). Histochemical staining of the adjacent sections with X-gal to illustrate the expression of the LacZ reporter gene in 3616UB also showed no evidence of viral infection other than a single blue cell at the needle track (data not shown). Brain sections from positive control mice that were injected with strain F, however, showed infected cells concentrated near the needle track at 24 hours post infection (FIG. 7B).

What is claimed is:

1. A herpes simplex virus vector for inhibiting or treating a malignant brain tumor, malignant leptomeningeal breast tumor, or hemangiosarcoma, wherein the genome of said vector contains alterations in both (i) the gamma 34.5 gene and (ii) uracil DNA glycosylase (UNG) gene, wherein said alterations prevent the expression of said genes or render the expressed products of said genes nonfunctional when a cell is transfected with said vector.

2. The virus vector as recited in claim 1 wherein said herpes simplex virus genome is an HSV-1 genome.

3. The virus vector as recited in claim 1 wherein said UNG gene is disrupted by the insertion of an about 1000 to about 5000 base pair Xba I fragment, containing the LacZ gene sequence, in the UNG gene of HSV-1.

4. A method of preparing the replication-competent herpes simplex virus vector of claim 1, said method comprising the steps of: (A) isolating a viral genome of a herpes simplex virus; and (B) permanently altering said genome so that neither a functional 34.5 gene product nor a functional uracil DNA glycosylase is expressed when a cell is transfected with said vector and the virus (1) is sensitive to antiviral agents and (2) kills tumor cells.

5. The method of claim 4, wherein said herpes simplex virus is HSV-1.

6. The method of claim 4, wherein said herpes simplex virus is HSV-2.

7. The method as recited in claim 4 wherein said herpes simplex virus comprises a UNG (UL2) gene having a LacZ gene in the reading frame between a first and a last codon of a coding sequence of said UNG gene.

TABLE 2

Viral toxicity in healthy murine brain tissue as measured by herpetic encephalitis.

| VIRUS | $PFU/LD_{50}$* | Survivors** | |
|---|---|---|---|
| | | Swiss Webster | CB17 SCID |
| 3616UB | $>1 \times 10^8$ | 6/6 | 6/6 |
| R3616 | $>2 \times 10^7$ | 5/6 | 6/6 |
| F | $5 \times 10^4$ | 0/6 | 0/6 |

*$PFU/LD_{50}$ ratios were established using the method of Reed and Muench (1938), following injection of groups of 6 Swiss Webster mice with serial 10-fold dilutions of viral stocks.
**Groups of 6 mice were injected with the highest attainable titers of the indicated viruses and observed for up to 30 days for the development of fatal encephalitis.

\* \* \* \* \*

UNITED STATES PATENT AND TRADEMARK OFFICE
CERTIFICATE OF CORRECTION

PATENT NO. : 6,509,020 B1
DATED : January 21, 2003
INVENTOR(S) : Richard Brent Pyles et al.

It is certified that error appears in the above-identified patent and that said Letters Patent is hereby corrected as shown below:

Title page, Item [54] and Column 1, line 2,
Title "REPLICATION-COMPETENT HERPES SIMPLEX VIRUS" should read
-- REPLICATION-COMPETENT HERPES SIMPLEX VIRUSES --.

Column 1,
Line 11, "1987" should read -- 1997 --.
Line 20, "invention relates to a mutated" should read -- invention relates to viruses --.
Line 25, "herpesvirus strains, vital vaccines" should read -- herpes virus strains, viral vaccines --.
Lines 48, 61, and 62, ":" should read -- ; --.

Column 2,
Lines 20, 26, and 27, ":" should read -- ; --.
Lines 30, 34, and 35, "." should read -- , --.
Line 59, "Herpes simplex" should read -- (Herpes simplex --.

Column 3,
Line 46, "the a uracil DNA" should read -- the uracil DNA --.
Line 58, "colon cancer cells lymphoma" should read -- colon cancer cells, lymphoma --.

Column 4,
Line 10, ":" should read -- ; --.
Line 20, "the a uracil DNA" should read --- the uracil DNA --.
Line 31, ":" should read -- ; --.
Line 37, "It should be understood however, that" should read -- It should be understood, however, that --.

Column 5,
Line 35, "culture also Was histochemically stained" should read -- culture also was histochemically stained --.
Line 57, "xenog raft" should read -- xenograft --.

Column 7,
Line 35, "1776 (McKie" should read -- 1776 [(McKie --.
Line 39, "." should read -- , --.
Line 56, "." should read -- , --.

Column 8,
Line 48, ":" should read -- ; --.

UNITED STATES PATENT AND TRADEMARK OFFICE
CERTIFICATE OF CORRECTION

PATENT NO. : 6,509,020 B1
DATED : January 21, 2003
INVENTOR(S) : Richard Brent Pyles et al.

It is certified that error appears in the above-identified patent and that said Letters Patent is hereby corrected as shown below:

Column 9,
Line 21, "end of thee" should read -- end of the --.
Line 40, ":" should read -- ; --.
Line 49, "30;" should read -- 30: --.
Line 51, "Breakefield" should read -- Breakfield --.
Line 57, ":" should read -- ; --.
Line 67, "Int'l Med. 11:893" should read -- It'l Med. 111:893 --.

Column 10,
Line 48, "populations May be" should read -- populations may be --.
Line 64, "9-92-hydroxyethoxy -methyl)guanine." should
read -- 9-(2-hydroxyethoxy-methyl)guanine. --.

Column 11,
Line 26, "." should read -- , --.

Column 12,
Line 23, "anti tumor" should read -- anti-tumor --.
Line 56, "include water, aqueous solutions saline solutions," should read
-- include waters, aqueous solutions, saline solutions, --.
Line 63, "the herpes simplex, virus vector would" should read -- the herpes simplex virus vector would --.
Line 65, ":" should read -- ; --.

Column 13,
Line 3, "indent" should read -- ingredient --.
Line 29, "clinicians discretion to treat" should read -- clinician's discretion to treat --.
Line 34, "raiotherapy" should read -- radiotherapy --.
Line 58, "synthesize antibodies; and degree of" should read -- synthesize antibodies, and degree of --.
Line 65, "standard surgery radiotherapy and chemotherapy" should read -- standard surgery, radiotherapy, and chemotherapy --.

Column 14,
Line 16, "and virus will inoculated in the resected tumor" should read -- and virus will be inoculated in the resected tumor --.
Line 26, "vital" should read -- viral --.
Line 47, "through a Nalgene 0.45 mu m filter sampled refiltered through a" should read -- through a Nalgene 0.45 mu m filter, sampled, refiltered through a --.

UNITED STATES PATENT AND TRADEMARK OFFICE
CERTIFICATE OF CORRECTION

PATENT NO.     : 6,509,020 B1
DATED          : January 21, 2003
INVENTOR(S)    : Richard Brent Pyles et al.

It is certified that error appears in the above-identified patent and that said Letters Patent is hereby corrected as shown below:

Column 15,
Line 12, "(Gaithersburg. MD)" should read -- (Gaithersburg, MD) --.
Line 19, "35-335.)" should read -- 325-335.) --.
Line 23, "human plasma serum nerve growth factor and fUdR at" should read -- human plasma serum, nerve growth factor and fUdR at --.
Line 35, "infected cells And then titered using" should read -- infected cells and then titered using --.

Column 16,
Line 5, "for 24 hours." should read -- for 2-4 hours. --.
Line 9, "(20-22 gm), female. CB 17" should read -- (20-22 gm), female, CB 17 --.
Line 23, "Groups of 6 mice were injected following Metofane anesthesia, in the left" should read -- Groups of 6 mice were injected, following Metofane anesthesia, in the left --.
Line 28, "To directly assess viral replication in healthy brain tissues. CB 17 SCID mice were" should read -- To directly assess viral replication in healthy brain tissues, CB 17 SCID mice were --.
Line 53, "3616UBI" should read -- 3616UB --.

Column 17,
Line 11, "Cold Spring Harbor. N.Y.)" should read -- Cold Spring Harbor, N.Y.) --.
Lines 29-30(Science 252. 854-856: Nature MEd.1. 938-943.)." should read -- Science 252, 854-856; Nature Med. 1, 938-943.) --.

Column 18,
Line 3, "To generate the viral multiple-mutant, 3616UB the" should read -- To generate the viral multiple-mutant, 3516UB, the --.
Line 53, "In each of the cultured cell types examined strain" should read -- In each of the cultured cell types examined, strain --.

Column 19,
Line 28, "cultures" should read -- cultured --.
Line 61, "(FIG. 4A & B)" should read -- (FIGS. 4A & B) --.

Column 20,
Line 23, "." should read -- , --.

UNITED STATES PATENT AND TRADEMARK OFFICE
CERTIFICATE OF CORRECTION

PATENT NO.     : 6,509,020 B1
DATED          : January 21, 2003
INVENTOR(S)    : Richard Brent Pyles et al.

It is certified that error appears in the above-identified patent and that said Letters Patent is hereby corrected as shown below:

Column 21,
Line 8, "FIG. 6A and 6B)." should read -- FIGS. 6A and 6B). --.
Line 22, ":" should read -- ; --.
Line 36, ":" should read -- ; --.

Signed and Sealed this

Twenty-sixth Day of August, 2003

JAMES E. ROGAN
*Director of the United States Patent and Trademark Office*